United States Patent [19]
Belousov et al.

[11] 4,116,778
[45] Sep. 26, 1978

[54] PLANT FOR CONTINUOUS CULTIVATION OF MICROORGANISMS

[76] Inventors: Viktor Vasilievich Belousov, ulitsa akademika Pavlova, 7, korpus 9, kv. 33, Moscow; Vadim Moiseevich Glazer, ulitsa Mayakovskogi, 8, kv. 50, Zhukovsy Moskovskoi oblasti; Sergei Vasilievich Shestakov, ulitsa Garibaldi, 15, korpus 1, kv. 100, Moscow, all of U.S.S.R.

[21] Appl. No.: 715,902

[22] Filed: Aug. 19, 1976

Related U.S. Application Data

[63] Continuation of Ser. No. 432,334, Jan. 10, 1974, abandoned.

[51] Int. Cl.² .............................................. C12B 1/00
[52] U.S. Cl. .................................. 195/139; 195/115; 195/142; 195/143
[58] Field of Search ............... 195/139, 140, 141, 142, 195/143, 115, 109

[56] References Cited

U.S. PATENT DOCUMENTS

| | | | |
|---|---|---|---|
| 2,635,070 | 4/1953 | Gordon et al. | 195/141 X |
| 3,419,473 | 12/1968 | Dawson | 195/115 X |
| 3,717,552 | 2/1973 | Hondermarck et al. | 195/143 X |

*Primary Examiner*—R. B. Penland
*Attorney, Agent, or Firm*—Haseltine, Lake, & Waters

[57] ABSTRACT

Disclosure is made of a plant for continuous cultivation of microorganisms.

The plant comprises a closed recirculation circuit made up by a fermenter, a pump and a process parameter measuring unit connected in series by means of an annular duct. The plant also comprises a container for storing a nutrient medium and a finished product collector having a supply line and an overflow connection, respectively. Down-stream of the measuring unit, the annular duct has two locking means; connected to the portion of the duct between the locking means are the supply line and the overflow connection, which accounts for equal volumes of a nutrient medium introduced into the recirculation circuit and of a suspension of microorganisms which is simultaneously discharged therefrom.

3 Claims, 2 Drawing Figures

PLANT FOR CONTINUOUS CULTIVATION OF MICROORGANISMS

This application is a continuation of our earlier filed co-pending: application Ser. No. 432,334 filed Jan. 10, 1974 and now abandoned.

FIELD OF THE INVENTION

The present invention relates to plants used in microbiology and, more particularly, to plants for continuous cultivation of microorganisms.

PRIOR ART

Known at present are plants for continuous cultivation of microorganisms produced by a number of companies in different countries, including the Marubishi of Japan, the Biotek of Sweden, the Chemap of Switzerland and the New Brunswick of the U.S. All these plants are similar in design.

A plant of the foregoing type comprises a recirculation circuit made up by a fermenter, a pump and a process parameter measuring unit, all being connected by means of an annular duct. The plant also comprises a container for storing a nutrient medium which is fed into the fermenter via a supply line with the aid of a metering pump. Inside the fermenter there is an overflow connection, one end thereof is secured at the level of the mirror of a microorganism suspension found in the fermenter. The second end of the overflow connection is connected to a collector for the microorganism suspension. The metering pump and the process parameter measuring unit are connected to a program control unit.

The plant operates as follows.

The nutrient medium is supplied, in a required quantity, to the fermenter and is inoculated with a germ culture. In the course of growth of microorganisms, the microorganism suspension is continuously made to circulate through the recirculation circuit by the pump. The metering pump is disconnected at this stage of the process.

When the density of the microorganism suspension reaches a preset value, the optical density transducer incorporated into the process parameter measuring unit sends a signal to the program control unit which actuates the metering pump, so that the nutrient medium starts being supplied from the container, where it is stored, to the fermenter.

At the initial stage of the process, the upper, open end of the overflow connection and the mirror of the microorganism suspension inside the fermenter are found at the same level; as the nutrient medium is being added to the microorganism suspension in the fermenter, the latter is discharged via the opening of the overflow connection into the collector for the microorganism suspension.

When the density of the microorganism suspension falls below the preset limit, due to the addition of the nutrient medium, the optical density transducer incorporated into the process parameter measuring unit sends a signal to the program control unit which switches off the metering pump. No nutrient medium is then supplied to the fermenter. The operating cycle is then repeated.

In the foregoing plant, the rate of the supply of the nutrient medium is set by the pump; the discharge depends upon the rise of the liquid column above the open end of the overflow connection. In this plant, it is impossible to achieve strict equality between the rate of the supply of the nutrient medium to the fermenter and that of the discharge of the microorganism suspension therefrom, which is due to a small value of the ratio between the height of the liquid column above the open end of the overflow connection and the area of the suspension mirror, as well as to the intensive stirring of the microorganism suspension resulting in irregular fluctuation of the suspension mirror in relation to the open end of the overflow connection and in an untimely discharge of the suspension.

In addition, the foregoing plant does not permit of the use of media containing heterogenic components, as these clog the overflow connection. These include flour, bran, vegetable mash and others, which, as a rule, are part of nutrient media used for industrial cultivation of microorganisms.

For the same reason, plants of the above type cannot be used for continuous cultivation of actonimycetes, mycelium funghi and filamentous algae which also display heterogenic distribution in a nutrient medium.

Also known in the art is a plant for continuous cultivation of microorganisms, comprising a closed recirculation circuit made up by a fermenter, a pump and a process parameter measuring unit, all being interconnected by means of an annular duct, and also comprising a container for storing a nutrient medium and a collector for a microorganism suspension.

The container for storing a nutrient medium communicates with the fermenter via a supply line having a locking means, through which the nutrient medium is fed to the fermenter with the aid of a metering pump.

From the annular duct, the microorganism suspension is supplied to an overflow connection provided with a shut-off valve and is discharged from the latter into a collector for the microorganism suspension by means of the metering pump.

The measuring unit, the locking devices and the metering pump are connected to a program control unit.

The above-mentioned plant operates in the following manner.

From the storage container, the nutrient medium is supplied, in a required quantity, to the fermenter where it is inoculated with a selected germ culture. In the period of the germ culture growth, the nutrient medium containing microorganisms and referred to as the microorganism suspension continuously circulates with the aid of the pump through the recirculation circuit. As this takes place, the locking means of the overflow connection and the supply line are closed, the metering pump is switched off and no signal is sent to the program control unit by the optical density transducer incorporated into the process parameter measuring unit. When the density of the microorganism suspension reaches a predetermined value, the optical density transducer sends a signal to the program control unit which opens the locking means of the overflow connection and of the supply line and actuates the metering pump, the latter supplying a portion of the nutrient medium to the fermenter via the supply line and simultaneously discharging a portion of the microorganism suspension from the annular duct via the overflow connection.

The metering pump is provided with a special attachment for preliminary balancing of flow rates in the overflow connection and the supply line, which before the start of the operation balances said flow rates.

When the density of the microorganism suspension falls below a preset value due to the additional thereto of a fresh portion of the nutrient medium, the optical density transducer stops sending signals to the program control unit which, in turn, switches off the metering pump and closes the locking means of the overflow connection and the supply line. The operating cycle is then repeated.

The sine qua non condition for continuous cultivation of microorganisms is the accurate balancing of the rate of the introduction of the nutrient medium into the recirculation circuit and that of the discharge therefrom of the microorganism suspension.

In the known plant for continuous cultivation of microorganisms, the equality of the rate of the introduction of the nutrient medium into the recirculation circuit and of that of the discharge therefrom of the microorganism suspension is to be attained by preliminary balancing of the flow rates in the supply line and the overflow connection, i.e. in two pipelines that do not communicate with each other, which is practically impossible. Even a minor unbalance of the flow rates disturbs the process of continuous cultivation of microorganisms, which disturbance is especially pronounced in the course of prolonged operation of the plant.

The use in the known plant of a special attachment for preliminary balancing of the flow rates in the supply line and the overflow connection makes the plant considerably more complicated without making equal the rates of the supply of the nutrient medium and the discharge of the microorganism suspension.

As a result of the intensive stirring of the microorganism suspension in the known plant, which is done in the fermenter, the suspension contains many air bubbles which, passing through the process parameter measuring unit, distort the values of the parameters being measured. This result in unnecessary signals sent to the program control unit which responds to all signals from the process parameter measuring unit, thus making errors in the supply of the nutrient medium and the discharge of the microorganism suspension.

By getting into the overflow connection, air bubbles upset the balance between the rates of the supply of the nutrient medium and the discharge of the microorganism suspension.

SUMMARY OF THE INVENTION

It is an object of the present invention to provide a plant for continuous cultivation of microorganisms which makes it possible to continuously obtain a suspension of microorganisms at the same preset stage of maturity.

It is another object of the present invention to provide a simpler and more reliable plant as compared to the known ones.

To attain the foregoing and other objects of the present invention, a plant for continuous cultivation of microorganisms is proposed, comprising a closed recirculation circuit made up by a fermenter, a pump and a process parameter measuring unit, all being connected by means of an annular duct, as well as a container for storing a nutrient medium connected via a supply line to the recirculation circuit which is also connected to a collector for a microorganism suspension via an overflow connection; according to the invention, the annular duct of the plant is provided with two locking means, connected between which to the duct are the supply line and the overflow connection; as a result, the volumes of the nutrient medium introduced into the recirculation circuit and of the microorganism suspension discharged simultaneously therefrom are equal.

The connection of the supply line and the overflow connection to a portion of the annular duct ensures their communication with each other, whereas the fact that said portion of the duct is found between the locking means makes for an indissoluble link between the introduction of a portion of the nutrient medium into the recirculation circuit and the discharge therefrom of an equal portion of the microorganism suspension. That, in turn, makes for a stable balance of the flow rates of the nutrient medium introduced into the recirculation circuit and the suspension of microorganisms discharged therefrom in the course of the plant's operation.

In accordance with the invention, installed at the portion of the recirculation circuit, found between the fermenter and the process parameter measuring unit, there may be a gas bubble separator connected by means of a by-pass pipe to the recirculation circuit downstream of the portion with the locking means.

The provision of the recirculation circuit with the gas bubble separator with a by-pass pipe at the portion between the fermenter and the process parameter measuring unit has made it possible, in the first place, to prevent gas bubbles from getting into the process parameter measuring unit and rule out distortions in the values of the parameters being measured, thereby ensuring timely switching on and off of the metering pump which introduces the nutrient medium into the recirculation circuit and discharges the suspension of microorganisms therefrom; in the second place, that has made it possible to prevent gas bubbles from getting into the portion of the annular duct found between the locking means, where said bubbles could disturb the balance of the volumes of the nutrient medium being supplied and of the suspension of microorganisms being discharged.

In accordance with the invention, the by-pass pipe may be connected to the annular duct upstream of the portion with the locking means by means of a connecting pipe provided with a shut-off valve.

Connecting the by-pass pipe by means of the connecting pipe to the portion of the annular duct upstream of the portion with the locking means has made it possible to ensure continuous circulation of the microorganism suspension through the process parameter measuring unit at the stage when the portion of the annular duct, connected whereto are the overflow connection and the supply line, is blocked off by the locking means and thus ensure continuous control of the density of the suspension of microorganisms in the recirculation circuit.

The fact that the balance between the rate of the introduction of the nutrient medium into the recirculation circuit and that of the discharge of the microorganism suspension therefrom is achieved without any additional attachment makes the proposed plant simpler in design and more reliable as compared to the known plants.

BRIEF DESCRIPTION OF THE DRAWINGS

The present invention will hereinafter be explained in greater detail with reference to the accompanying drawings, wherein.

DETAILED DESCRIPTION

Figure 1:
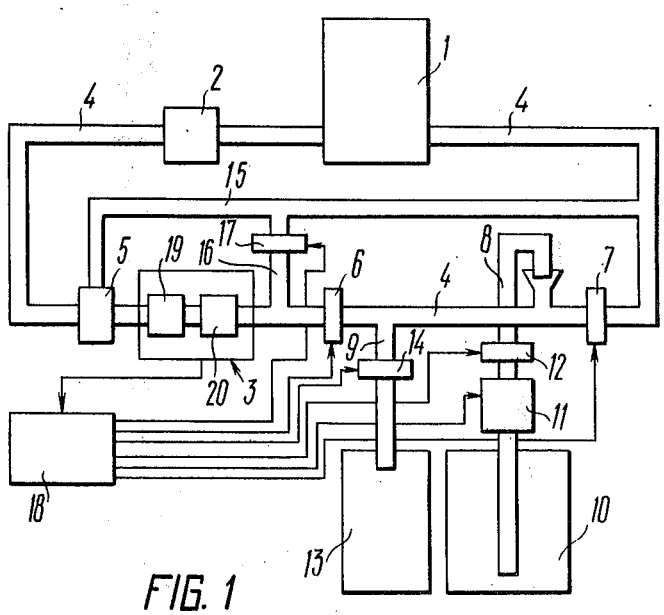
FIG. 1 is a diagram of a plant for continuous cultivation of microorganisms, wherein the process parameter measuring unit is arranged in the recirculation circuit.

Referring now to FIG. 1, the plant for continuous cultivation of microorganisms comprises a closed recirculation circuit for continuous circulation therethrough of a suspension of microorganisms, made up by a fermenter 1, a pump 2 and a process parameter measuring unit 3, all being connected by means of an annular duct 4.

Installed between the fermenter 1 and the process parameter measuring unit 3 is a gas bubble separator 5.

Downstream of the process parameter measuring unit 3, the annular duct 4 has two locking means 6 and 7; connected to the annular duct between said locking means are a supply line 8 and an overflow connection 9.

The supply line 8 communicates the annular duct 4 with a container 10 for storing a nutrient medium. The supply line 8 has a metering pump 11 and a shut-off valve 12.

The annular duct 4 is connected by means of the overflow connection 9 to a collector 13 for a suspension of microorganisms. The overflow connection 9 has a shut-off valve 14.

The gas bubble separator 5 is connected to the annular duct 4 downstream of the portion with the locking means 6 and 7 by means of a by-pass pipe 15, wherethrough gas bubbles with a portion of the suspension of microorganisms are directed to the annular duct 4.

The by-pass pipe is connected to the portion of the annular duct 4 found between the process parameter measuring unit 3 and the locking means 6 by means of a connecting pipe 16 having a shut-off valve 17.

The process parameter measuring unit 3, the locking means 6 and 7, the shut-off valves 12, 14 and 17 and the metering pump 11 are electrically connected to a program control unit 18.

The fermenter 1 is a container designed for cultivation of microorganisms introduced into a nutrient medium contained therein.

The pump 2 is meant for continuous circulation of the suspension of microorganisms through the recirculation pipeline and the by-pass pipe 15.

The process parameter measuring unit 3 consists of a flow cell 19 and a flow tank 20 connected sequentially.

The flow cell 19 is designed for measuring the temperature of the microorganism suspension, as well as the latter's pH, the partial pressure of oxygen dissolved therein and the oxidation-reduction potential.

The flow tank 20 is meant for measuring the optical density of the microorganism suspension.

The process parameter measuring unit 3 is electrically connected to the program control unit 18.

Figure 2:
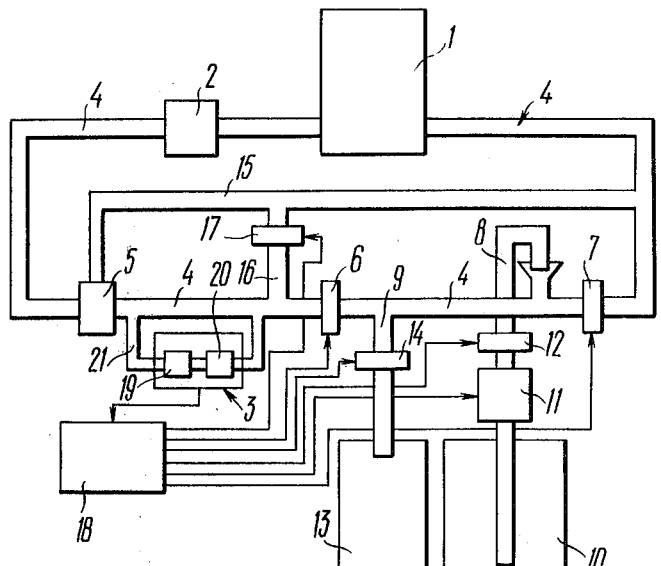
FIG. 2 is a diagram of a plant, wherein the process parameter measuring unit is arranged in an additional bypass pipe connected to the annular duct.

In case the plant is used for industrial cultivation of microorganisms, when the flow rate of the microorganism suspension in the annular duct is great, the process parameter measuring unit 3 (FIG. 2) is arranged in an additional by-pass pipe 21 connected in parallel with the annular duct 4.

The plant operates as follows.

Before the start of the operation the plant is sterilized after which the container 10 for storing a nutrient medium is filled with a sterile nutrient medium. From the container 10, the nutrient medium is then fed through the supply line 8 with the aid of continuously operating metering pump 11 and via the annular duct 4 to the fermenter 1, filling the latter up to a required level. After that the continuous supply of the nutrient medium to the fermenter is stopped, and the metering pump 11 is connected to the program control unit 18.

The nutrient medium is then warmed up to reach a temperature which is optimum for the growth of a given germ culture, the warming up being accompanied by intensive stirring and oxygenation of the nutrient medium.

The nutrient medium in the fermenter 1 is then inoculated with a selected germ culture.

After that the pump 2 is brought into action, ensuring continuous circulation of the microorganism suspension through the recirculation circuit.

During the period of growth of the germ culture, the metering pump 11 is out of action, the locking means 6 and 7 are open, and the shut-off valves 12, 14 and 17 are closed.

Upon entering the separator 5, the microorganism suspension is divided into two flows; one flow of the microorganism suspension, containing gas bubbles, is directed through the by-pass pipe 15 into the annular duct 4, whereas the other, free of gas bubbles, is directed into the flow cell 19 and further on into the flow tank 20 communicating with the latter; the cell 19 is used for measuring the temperature of the suspension of microorganisms, as well as the suspension's pH, the partial pressure of oxygen dissolved therein and the oxidation-reduction potential thereof, whereas the flow tank 20 is used to measure the optical density of the suspension of microorganisms.

When the optical density of the microorganism suspension reaches a predetermined value, the flow tank 20 of the process parameter measuring unit 3 sends a signal to the program control unit 18 which, in turn, sends signals to the locking means 6 and 7, the shut-off valves 12, 14 and 17 and the metering pump 11 which are all electrically connected to the program control unit. This results in four successively performed operations: the opening of the shut-off valve 17, the closing of the locking means 6 and 7, the opening of the shut-off valves 12 and 14 and the actuation of the metering pump 11.

As the locking means 6 and 7 are closed and the valve 17 is opened, the suspension of microorganisms, after the process parameter measuring unit 3, is directed through the connecting pipe 16, via the by-pass pipe 15 and the annular duct 4 to the fermenter 1. Simultaneously, the metering pump 11 supplies via the supply line 8 a measured portion of fresh nutrient medium to the annular duct 4, ousting therefrom an equal volume of the microorganism suspension which is directed through the overflow connection 9 to the collector 13 for microorganism suspension. The volume of the portion of fresh nutrient medium must be less than that of the portion of the annular duct 4 between the connection thereto of the overflow connection 9 and the supply line 8.

The program control unit 18 then performs the abovementioned operation is reverse order: the metering pump 11 is switched off, the shut-off valves 12 and 14 are closed, the locking means 6 and 7 are opened, and the shut-off valve 17 is closed.

As the locking means 6 and 7 are opened, the portion of the nutrient medium introduced into the annular duct 4 is carried with the flow of the circulating suspension of microorganisms via the opened locking means 6 and 7 and the portion of the annular duct 4 therebetween to the fermenter 1 where the suspension of microorganisms is diluted in the fresh portion of the nutrient medium.

In case the dilution of the microorganism suspension is not adequate, the process parameter measuring unit 3 continues sending signals to the program control unit, ensuring thereby the introduction of fresh portions of the nutrient medium into the recirculation circuit until the density of the suspension of microorganisms therein is below a preset value.

The plant's operating cycle is then repeated.

If the process parameter measuring unit 3 is arranged in the additional by-pass pipe 21 (FIG. 2) connected in parallel with the annular duct 4, a portion of the suspension of microorganisms is fed from the annular duct 4 via the additional by-pass pipe 21 to the cell 19 and the flow tank 20 communicating with the latter, both the cell and the tank being arranged in the additional by-pass pipe 21; from the cell and the tank, the microorganism suspension returns to the annular duct 4. In this case the mainstream suspension flow is through the annular duct 4.

Subsequently the plant operates as has been described hereinabove.

The proposed plant is simpler in design as compared to the known plants and ensures in the course of operation a stable balance between the rate of the introduction of the nutrient medium into the recirculation circuit and that of the discharge of the microorganism suspension therefrom, which makes it possible to obtain, in the course of a prolonged period of time, a suspension of microorganisms at a preset stange of growth.

The elimination of errors in the system of measuring the parameters of the process has made possible automatic control of the process of continuous production of a suspension of microorganisms at a preset stage of growth.

The proposed plant makes it possible to continuously obtain suspensions of any microorganisms and cultivate microorganisms in all kinds of nutrient media used in industry and research.

What is claimed is:

1. A plant for the continuous cultivation of microorganisms, comprising a fermenter for growing a suspension of microorganisms, which comprises a nutrient medium with a corresponding culture of microorganisms added thereto, said fermenter having an inlet and outlet, an annular duct having one end connected to the inlet into said fermenter and a second end connected to the outlet thereof for circulating the suspension of microorganisms therethrough; a recirculating pump installed in said annular duct downstream of said fermenter, and through which the suspension of microorganisms is pumped for effecting recirculation thereof; a process parameter measuring unit installed in said annular duct downstream of said recirculating pump; said fermenter, said recirculating pump, and said process parameter measuring unit being connected in series by said annular duct to form a recirculating circuit for continuously circulating the suspension of microorganisms therethrough; two locking means spaced apart in said annular duct downstream of said process parameter measuring unit; a supply line connected to the section of said annular duct between said locking means; a nutrient medium storage container connected to said supply line; an overflow connection connected to the section of said annular duct between said locking means for withdrawing the suspension of microorganisms from the section of said annular duct between said locking means; a microorganism suspension collector connected to said overflow connection; a metering pump located in said supply line for supplying measured quantities of the nutrient medium from said nutrient medium storage container to the section of the annular duct between said locking means and for; discharging therefrom an equal volume of the suspension of microorganisms into said microorganism suspension collector.

2. A plant for the continuous cultivation of microorganisms as claimed in claim 1, comprising a gas bubble separator located in the section of said recirculating circuit between said fermenter and said process parameter measuring unit for completely removing gas bubbles from the suspension of microorganisms which bubble free suspension is introduced into said process parameter measuring unit and subsequently into the section of said annular duct between said locking means; a by-pass pipeline connecting said gas bubble separator to said recirculating circuit located downstream of the section of said annular duct which accommodates said locking means.

3. A plant for the continuous cultivation of microorganisms as claimed in claim 2 further comprising a connecting pipe including a shut-off valve connecting said by-pass pipeline to the section of said annular duct located upstream of said process parameter measuring unit and the section of said annular duct which accommodates said first locking means.

* * * * *